(12) United States Patent
Truckai et al.

(10) Patent No.: US 7,981,113 B2
(45) Date of Patent: Jul. 19, 2011

(54) ELECTROSURGICAL INSTRUMENT

(75) Inventors: Csaba Truckai, Saratoga, CA (US);
John H. Shadduck, Tiburon, CA (US);
Bruno Strul, Portola Valley, CA (US)

(73) Assignee: Surgrx, Inc., Redwood City, CA (US)

( * ) Notice: Subject to any disclaimer, the term of this patent is extended or adjusted under 35 U.S.C. 154(b) by 520 days.

(21) Appl. No.: 12/098,560

(22) Filed: Apr. 7, 2008

(65) Prior Publication Data

US 2008/0188851 A1 Aug. 7, 2008

Related U.S. Application Data

(60) Division of application No. 11/673,889, filed on Feb. 12, 2007, now Pat. No. 7,381,209, which is a division of application No. 10/934,755, filed on Sep. 3, 2004, now Pat. No. 7,189,233, and a continuation-in-part of application No. 10/351,449, filed on Jan. 22, 2003, now Pat. No. 7,112,201, and a continuation-in-part of application No. 10/032,867, filed on Oct. 22, 2001, now Pat. No. 6,929,644.

(60) Provisional application No. 60/500,746, filed on Sep. 4, 2003, provisional application No. 60/351,517, filed on Jan. 22, 2002.

(51) Int. Cl.
*A61B 18/12* (2006.01)
(52) U.S. Cl. .............. 606/49; 606/41; 606/52
(58) Field of Classification Search .......... 606/41–52
See application file for complete search history.

(56) References Cited

U.S. PATENT DOCUMENTS

| 659,409 A | 10/1900 | Mosher |
| 1,586,645 A | 6/1926 | Bierman |
| 1,798,902 A | 3/1931 | Raney |
| 1,881,250 A | 10/1932 | Tomlinson |
| 2,031,682 A | 2/1936 | Wappler et al. |
| 3,651,811 A | 3/1972 | Hildebrandt et al. |
| 3,685,518 A | 8/1972 | Beuerle et al. |
| 3,730,188 A | 5/1973 | Ellman |
| 3,768,482 A | 10/1973 | Shaw |
| 3,826,263 A | 7/1974 | Cage et al. |
| 4,092,986 A | 6/1978 | Schneiderman |
| 4,198,957 A | 4/1980 | Cage et al. |
| 4,219,025 A | 8/1980 | Johnson |
| 4,231,371 A | 11/1980 | Lipp |
| 4,232,676 A | 11/1980 | Herczog |
| 4,271,838 A | 6/1981 | Lasner et al. |

(Continued)

FOREIGN PATENT DOCUMENTS

EP 0 341 446 A2 4/1989
(Continued)

OTHER PUBLICATIONS

Smith et al., "Electrosurgery in Otolaryngology—Head and Neck Surgery: Principles, Advances, and Complications," Laryngoscope 2001 May;111(5):769-80.
U.S. Appl. No. 60/347,382, filed Jan. 11, 2002, First Named Inventor: Csaba Truckai.

*Primary Examiner* — Henry M Johnson, III
*Assistant Examiner* — Aaron Roane
(74) *Attorney, Agent, or Firm* — Verne E. Kreger, Jr.

(57) ABSTRACT

An embodiment of the invention includes an electrosurgical jaw structure that carries cooperating PTC bodies in both series and parallel circuit components for controlled RF energy application to engaged tissue to effectively weld tissue.

17 Claims, 14 Drawing Sheets

U.S. PATENT DOCUMENTS

| | | | |
|---|---|---|---|
| 4,353,371 A | 10/1982 | Cosman | |
| 4,370,980 A | 2/1983 | Lottick | |
| 4,375,218 A | 3/1983 | Digeronimo | |
| 4,492,231 A | 1/1985 | Auth | |
| 4,590,934 A | 5/1986 | Malis et al. | |
| 4,608,981 A | 9/1986 | Rothfuss et al. | |
| 4,633,874 A | 1/1987 | Chow et al. | |
| 4,654,511 A | 3/1987 | Horsma et al. | |
| 4,655,216 A | 4/1987 | Tischer | |
| 4,671,274 A | 6/1987 | Sorochenko | |
| 4,691,703 A | 9/1987 | Auth et al. | |
| 4,763,669 A | 8/1988 | Jaeger | |
| 4,785,807 A | 11/1988 | Blanch | |
| 4,848,337 A | 7/1989 | Shaw et al. | |
| 4,850,353 A | 7/1989 | Stasz et al. | |
| 4,887,612 A | 12/1989 | Esser et al. | |
| 4,940,468 A | 7/1990 | Petillo | |
| 4,958,539 A | 9/1990 | Stasz et al. | |
| 4,969,885 A | 11/1990 | Farin | |
| 4,985,030 A | 1/1991 | Melzer et al. | |
| 5,009,656 A | 4/1991 | Reimels | |
| 5,057,106 A | 10/1991 | Kasevich et al. | |
| 5,057,107 A | 10/1991 | Parins et al. | |
| 5,085,659 A | 2/1992 | Rydell | |
| 5,104,025 A | 4/1992 | Main et al. | |
| 5,122,137 A | 6/1992 | Lennox | |
| 5,147,356 A | 9/1992 | Bhatta | |
| 5,147,357 A | 9/1992 | Rose et al. | |
| 5,151,102 A | 9/1992 | Kamiyama et al. | |
| 5,190,541 A | 3/1993 | Abele et al. | |
| 5,201,900 A | 4/1993 | Nardella | |
| 5,207,691 A | 5/1993 | Nardella | |
| 5,258,006 A | 11/1993 | Rydell et al. | |
| 5,267,998 A | 12/1993 | Hagen | |
| 5,269,780 A | 12/1993 | Roos | |
| 5,290,286 A | 3/1994 | Parins | |
| 5,306,280 A | 4/1994 | Bregen et al. | |
| 5,308,311 A | 5/1994 | Eggers et al. | |
| 5,324,289 A | 6/1994 | Eggers | |
| 5,336,221 A | 8/1994 | Anderson | |
| 5,360,428 A | 11/1994 | Hutchinson, Jr. | |
| 5,364,389 A | 11/1994 | Anderson | |
| 5,389,098 A | 2/1995 | Tsuruta et al. | |
| 5,403,312 A | 4/1995 | Yates et al. | |
| 5,417,687 A | 5/1995 | Nardella et al. | |
| 5,443,463 A | 8/1995 | Stern et al. | |
| 5,445,638 A | 8/1995 | Rydell et al. | |
| 5,451,224 A | 9/1995 | Goble et al. | |
| 5,458,598 A | 10/1995 | Feinberg et al. | |
| 5,480,397 A | 1/1996 | Eggers et al. | |
| 5,480,398 A | 1/1996 | Eggers | |
| 5,507,106 A | 4/1996 | Fox | |
| 5,531,744 A | 7/1996 | Nardella et al. | |
| 5,571,153 A | 11/1996 | Wallsten | |
| 5,573,535 A | 11/1996 | Viklund | |
| 5,593,406 A | 1/1997 | Eggers et al. | |
| 5,611,798 A | 3/1997 | Eggers | |
| 5,624,452 A | 4/1997 | Yates | |
| 5,674,220 A | 10/1997 | Fox et al. | |
| 5,693,051 A | 12/1997 | Schulze et al. | |
| 5,716,366 A | 2/1998 | Yates | |
| 5,735,848 A | 4/1998 | Yates et al. | |
| 5,755,717 A | 5/1998 | Yates et al. | |
| 5,766,166 A | 6/1998 | Hooven | |
| 5,776,130 A | 7/1998 | Buysse et al. | |
| 5,797,938 A | 8/1998 | Paraschal et al. | |
| 5,800,449 A | 9/1998 | Wales | |
| 5,807,392 A | 9/1998 | Eggers | |
| 5,833,690 A | 11/1998 | Yates et al. | |
| 5,891,142 A | 4/1999 | Eggers et al. | |
| 5,911,719 A | 6/1999 | Eggers | |
| 5,947,984 A | 9/1999 | Whipple | |
| 6,019,758 A | 2/2000 | Slater | |
| 6,030,384 A | 2/2000 | Nezhat | |
| 6,039,733 A | 3/2000 | Buysse et al. | |
| 6,074,389 A | 6/2000 | Levine et al. | |
| 6,086,586 A | 7/2000 | Hooven | |
| 6,113,598 A | 9/2000 | Baker | |
| 6,132,426 A | 10/2000 | Kroll | |
| 6,139,508 A | 10/2000 | Simpson et al. | |
| 6,152,923 A | 11/2000 | Ryan | |
| 6,162,220 A | 12/2000 | Nezhat | |
| 6,174,309 B1 | 1/2001 | Wrublewski et al. | |
| 6,176,857 B1 | 1/2001 | Ashley | |
| 6,179,834 B1 | 1/2001 | Buysse et al. | |
| 6,179,835 B1 | 1/2001 | Panescu et al. | |
| 6,179,837 B1 | 1/2001 | Hooven | |
| 6,187,003 B1 | 2/2001 | Buysse et al. | |
| 6,190,386 B1 | 2/2001 | Rydell | |
| 6,193,709 B1 | 2/2001 | Miyawaki et al. | |
| 6,270,497 B1 | 8/2001 | Sekino et al. | |
| 6,273,887 B1 | 8/2001 | Yamauchi et al. | |
| 6,277,117 B1 | 8/2001 | Tetzlaff et al. | |
| 6,296,640 B1 | 10/2001 | Wampler et al. | |
| 6,298,550 B1 | 10/2001 | Kirwan, Jr. | |
| 6,328,703 B1 | 12/2001 | Murakami | |
| 6,334,861 B1 | 1/2002 | Chandler et al. | |
| 6,350,264 B1 | 2/2002 | Hooven | |
| 6,352,536 B1 | 3/2002 | Buysse et al. | |
| 6,398,779 B1 | 6/2002 | Buysse et al. | |
| 6,409,725 B1 | 6/2002 | Khandkar et al. | |
| 6,451,018 B1 | 9/2002 | Lands et al. | |
| 6,458,128 B1 | 10/2002 | Schulze | |
| 6,458,130 B1 | 10/2002 | Frazier et al. | |
| 6,464,704 B2 | 10/2002 | Schmaltz | |
| 6,468,275 B1 | 10/2002 | Wampler et al. | |
| 6,492,629 B1 | 12/2002 | Sopory | |
| 6,500,176 B1 | 12/2002 | Truckai et al. | |
| 6,511,480 B1 | 1/2003 | Tetzlaff et al. | |
| 6,527,767 B2 | 3/2003 | Wang et al. | |
| 6,533,784 B2 | 3/2003 | Truckai et al. | |
| 6,554,829 B2 | 4/2003 | Schulze et al. | |
| 6,575,968 B1 | 6/2003 | Eggers et al. | |
| 6,585,735 B1 | 7/2003 | Frazier et al. | |
| 6,632,193 B1 | 10/2003 | Davison et al. | |
| 6,652,521 B2 | 11/2003 | Schulze | |
| 6,656,177 B2 | 12/2003 | Truckai et al. | |
| 6,773,409 B2 | 8/2004 | Truckai et al. | |
| 6,802,843 B2 | 10/2004 | Truckai et al. | |
| 6,843,789 B2 | 1/2005 | Goble | |
| 6,890,332 B2 | 5/2005 | Truckai et al. | |
| 6,893,435 B2 | 5/2005 | Goble | |
| 6,913,579 B2 | 7/2005 | Truckai et al. | |
| 6,926,716 B2 | 8/2005 | Baker et al. | |
| 6,929,644 B2 | 8/2005 | Truckai et al. | |
| 7,011,657 B2 | 3/2006 | Truckai et al. | |
| 7,041,102 B2 | 5/2006 | Truckai et al. | |
| 7,083,619 B2 | 8/2006 | Truckai et al. | |
| 7,112,201 B2 | 9/2006 | Truckai et al. | |
| 7,189,233 B2 | 3/2007 | Truckai et al. | |
| 7,309,849 B2 | 12/2007 | Truckai et al. | |
| 2002/0177848 A1 | 11/2002 | Truckai et al. | |
| 2003/0018327 A1 | 1/2003 | Truckai et al. | |
| 2003/0050635 A1 | 3/2003 | Truckai et al. | |
| 2003/0078573 A1 | 4/2003 | Truckai et al. | |
| 2003/0114851 A1 | 6/2003 | Truckai et al. | |
| 2003/0139741 A1 | 7/2003 | Goble et al. | |

FOREIGN PATENT DOCUMENTS

| | | |
|---|---|---|
| EP | 0 517 244 B1 | 3/1996 |
| EP | 0 518 230 B1 | 5/1996 |
| FR | 2536924 A1 | 6/1984 |
| FR | 2647683 A1 | 12/1990 |
| GB | 2037167 A | 7/1980 |
| GB | 2066104 A | 7/1981 |
| GB | 2133290 A | 4/1989 |
| GB | 2161082 A | 3/1996 |
| JP | 05-337129 | 12/1993 |
| JP | 10-033551 | 2/1998 |
| JP | 10-118092 | 5/1998 |
| JP | 2001-057302 | 2/2001 |
| JP | 2001-170069 | 6/2001 |
| SU | 342617 | 6/1984 |
| SU | 575103 | 5/1996 |
| WO | WO 94/24951 A1 | 7/1980 |
| WO | WO 94/24949 A1 | 7/1981 |
| WO | WO 93/08754 A1 | 5/1993 |

ELECTROSURGICAL INSTRUMENT

CROSS-REFERENCES TO RELATED APPLICATIONS

This application is a division of U.S. application Ser. No. 11/673,889, filed Feb. 12, 2007 (now U.S. Pat. No. 7,381,209), which is a divisional of U.S. application Ser. No. 10/934,755, filed Sep. 3, 2004 (now U.S. Pat. No. 7,189,233), which claims the benefit of U.S. Provisional Application No. 60/500,746, filed on Sep. 4, 2003, and is a Continuation-in-part of U.S. patent application Ser. No. 10/351,449, filed Jan. 22, 2003, titled Electrosurgical Instrument and Method of Use (now U.S. Pat. No. 7,112,201), which claimed the benefit of Provisional Application Nos. 60/351,517, filed on Jan. 22, 2002, and 60/366, 992, filed on Mar. 20, 2002, and was a continuation-in-part of application Ser. No. 10/032,867 filed Oct. 22, 2001, titled Electrosurgical Jaw Structure for Controlled Energy Delivery (now U.S. Pat. No. 6,929,644); the full disclosures of which are incorporated herein by reference.

BACKGROUND OF THE INVENTION

1. Field of the Invention

Embodiments of the invention relate to an electrosurgical instrument coupled to a radiofrequency generator, and more particularly to an electrosurgical jaw structure that is capable of modulating ohmic heating of engaged tissue for tissue welding or sealing purposes.

2. Description of the Background Art

In the prior art, various energy sources such as radiofrequency (RF) sources, ultrasound sources and lasers have been developed to coagulate, seal or join together tissues volumes in open and laparoscopic surgeries. The most important surgical application relates to sealing blood vessels which contain considerable fluid pressure therein. In general, no instrument working ends using any energy source have proven reliable in creating a "tissue weld" or "tissue fusion" that has very high strength immediately post-treatment. For this reason, the commercially available instruments, typically powered by RF or ultrasound, are mostly limited to use in sealing small blood vessels and tissues masses with microvasculature therein. The prior art RF devices also fail to provide seals with substantial strength in anatomic structures having walls with irregular or thick fibrous content, in bundles of disparate anatomic structures, in substantially thick anatomic structures, or in tissues with thick fascia layers (e.g., large diameter blood vessels).

In a basic bi-polar RF jaw arrangement, each face of opposing first and second jaws comprises an electrode and RF current flows across the captured tissue between the opposing polarity electrodes. Such prior art RF jaws that engage opposing sides of tissue typically cannot cause uniform thermal effects in the tissue—whether the captured tissue is thin or substantially thick. As RF energy density in tissue increases, the tissue surface becomes desiccated and resistant to additional ohmic heating. Localized tissue desiccation and charring can occur almost instantly as tissue impedance rises, which then can result in a non-uniform seal in the tissue. The typical prior art RF jaws can cause further undesirable effects by propagating RF density laterally from the engaged tissue thus causing unwanted collateral thermal damage.

The commercially available RF sealing instruments typically use one of two approaches to "control" RF energy delivery in tissue. In a first "power adjustment" approach, the RF system controller can rapidly adjust the level of total power delivered to the jaws' engagement surfaces in response to feedback circuitry coupled to the active electrodes that measures tissue impedance or electrode temperature. In a second "current-path directing" approach, the instrument jaws carry an electrode arrangement in which opposing polarity electrodes are spaced apart by an insulator material—which may cause current to flow within an extended path through captured tissue rather that simply between surfaces of the first and second jaws. Electrosurgical grasping instruments having jaws with electrically-isolated electrode arrangements in cooperating jaws faces were proposed by Yates et al. in U.S. Pat. Nos. 5,403,312; 5,735,848 and 5,833, 690.

The illustrations of the wall of a blood vessel in FIGS. 1A-1D are useful in understanding the limitations of prior art RF working ends for sealing tissue. FIG. 1B provides a graphic illustration of the opposing vessel walls portions $2a$ and $2b$ with the tissue divided into a grid with arbitrary micron dimensions—for example, the grid can represent 5 microns on each side of the targeted tissue. In order to create the most effective "weld" in tissue, each micron-dimensioned volume of tissue must be simultaneously elevated to the temperature needed to denature proteins therein. As will be described in more detail below, in order to create a "weld" in tissue, collagen and other protein molecules within an engaged tissue volume should be denatured by breaking the inter- and intra-molecular hydrogen bonds—followed by re-crosslinking on thermal relaxation to create a fused-together tissue mass. It can be easily understood that ohmic heating in tissue—if not uniform—can at best create localized spots of truly "welded" tissue. Such a non-uniformly denatured tissue volume still is "coagulated" and will prevent blood flow in small vasculature that contains little pressure. However, such non-uniformly denatured tissue will not create a seal with significant strength, for example in 2 mm. to 10 mm. arteries that contain high pressures.

Referring now to FIG. 1C, it is reasonable to ask whether the "power adjustment" approach to energy delivery is likely to cause a uniform temperature within every micron-scale tissue volume in the grid simultaneously—and maintain that temperature for a selected time interval. FIG. 1C shows the opposing vessel walls $2a$ and $2b$ being compressed with cut-away phantom views of opposing polarity electrodes on either side of the tissue. One advantage of such an electrode arrangement is that 100% of each jaw engagement surface comprises an "active" conductor of electrical current—thus no tissue is engaged by an insulator which theoretically would cause a dead spot (no ohmic heating) proximate to the insulator. FIG. 1C graphically depicts current "paths" p in the tissue at an arbitrary time interval that can be microseconds (μs) apart. Such current paths p would be random and constantly in flux—along transient most conductive pathways through the tissue between the opposing polarity electrodes. The thickness of the "paths" is intended to represent the constantly adjusting power levels. If one assumes that the duration of energy density along any current path p is within the microsecond range before finding a new conductive path—and the thermal relaxation time of tissue is the millisecond (ms) range, then what is the likelihood that such entirely random current paths will revisit and maintain each discrete micron-scale tissue volume at the targeted temperature before thermal relaxation? Since the hydration of tissue is constantly reduced during ohmic heating—any regions of more desiccated tissue will necessarily lose its ohmic heating and will be unable to be "welded" to adjacent tissue volumes. The "power adjustment" approach probably is useful in preventing rapid overall tissue desiccation. However, it is postulated that any approach that relies on entirely "random" current paths p in tissue—no matter the power level—cannot cause contemporaneous denaturation of tissue constituents in all engaged tissue volumes and thus cannot create an effective high-strength "weld" in tissue.

Referring now to FIG. 1D, it is possible to evaluate the second "current-path directing" approach to energy delivery in a jaw structure. FIG. 1D depicts vessel walls 2a and 2b engaged between opposing jaws surfaces with cut-away phantom views of opposing polarity (+) and (−) electrodes on each side of the engaged tissue. An insulator indicated at 10 is shown in cut-away view that electrically isolates the electrodes in the jaw. One significant disadvantage of using an insulator 10 in a jaw engagement surface is that no ohmic heating of tissue can be delivered directly to the tissue volume engaged by the insulator 10 (see FIG. 1D). The tissue that directly contacts the insulator 10 will only be ohmically heated when a current path p extends through the tissue between the spaced apart electrodes. FIG. 1D graphically depicts current paths p at any arbitrary time interval, for example in the μs range. Again, such current paths p will be random and in constant flux along transient conductive pathways.

This type of random, transient RF energy density in paths p through tissue, when any path may occur only for a microsecond interval, is not likely to uniformly denature proteins in the entire engaged tissue volume. It is believed that the "current-path directing" approach for tissue sealing can only accomplish tissue coagulation or seals with limited strength.

BRIEF SUMMARY OF THE INVENTION

Various embodiments of systems and methods of the invention relate to creating thermal "welds" or "fusion" within native tissue volumes. The alternative terms of tissue "welding" and tissue "fusion" are used interchangeably herein to describe thermal treatments of a targeted tissue volume that result in a substantially uniform fused-together tissue mass, for example in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof.

The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may not be fully understood. However, the authors have identified the parameters at which tissue welding can be accomplished. An effective "weld" as disclosed herein results from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

Various embodiments of the invention provide an electrosurgical jaw structure adapted for transecting captured tissue between the jaws and for contemporaneously welding the captured tissue margins with controlled application of RF energy. The jaw structure can comprise first and second opposing jaws that carry positive temperature coefficient (PTC) bodies for modulating RF energy delivery to the engaged tissue. In one embodiment the jaws can include first and second PTC bodies that define different temperature-impedance curves. Use of such first and second PTC bodies having different temperature impedance curves, allows for the control of the ohmic heating of tissue and the production of more uniform and higher strength welds than prior art RF sealing instruments In one embodiment, the electrosurgical jaws use first and second energy-delivery jaw surfaces coupled in series to an RF source, with a first jaw surface overlying and electrically coupled to a first PTC body, wherein the first jaw surface and first PTC body are also coupled in parallel to the RF source. The second surface can overlie a second PTC body or a portion of the second surface can comprise the second PTC body.

In another embodiment, the electrosurgical jaws comprise an electrosurgical instrument that uses first and second jaws defining first and second energy-application surfaces. The first surface comprises a first polarity electrode portion and an electrically coupled PTC portion within a first circuit portion connected to an RF source. The second surface comprises a second polarity electrode and an electrically coupled PTC portion within a second circuit portion connected to the RF source, wherein the first and second circuit portions are parallel and series respectively.

DETAILED DESCRIPTION OF THE INVENTION

Figure 2:
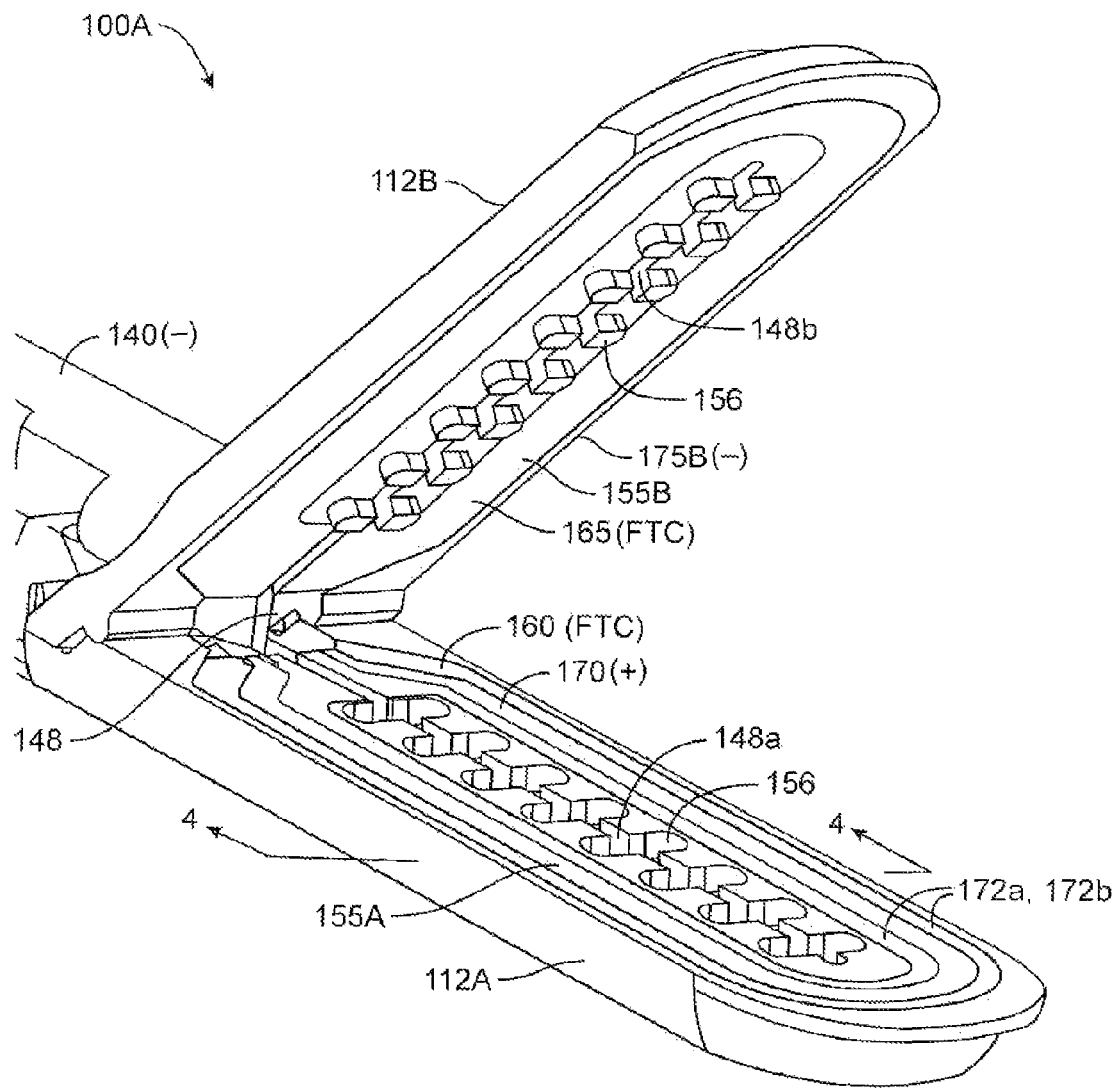
FIG. 2 is a perspective cut-away view of an exemplary Type "A" jaw structure for tissue welding and transection that carries first and second PTC energy delivery surfaces coupled to an RF source via series and parallel circuits for modulating ohmic heating in engaged tissue.
Figure 3:
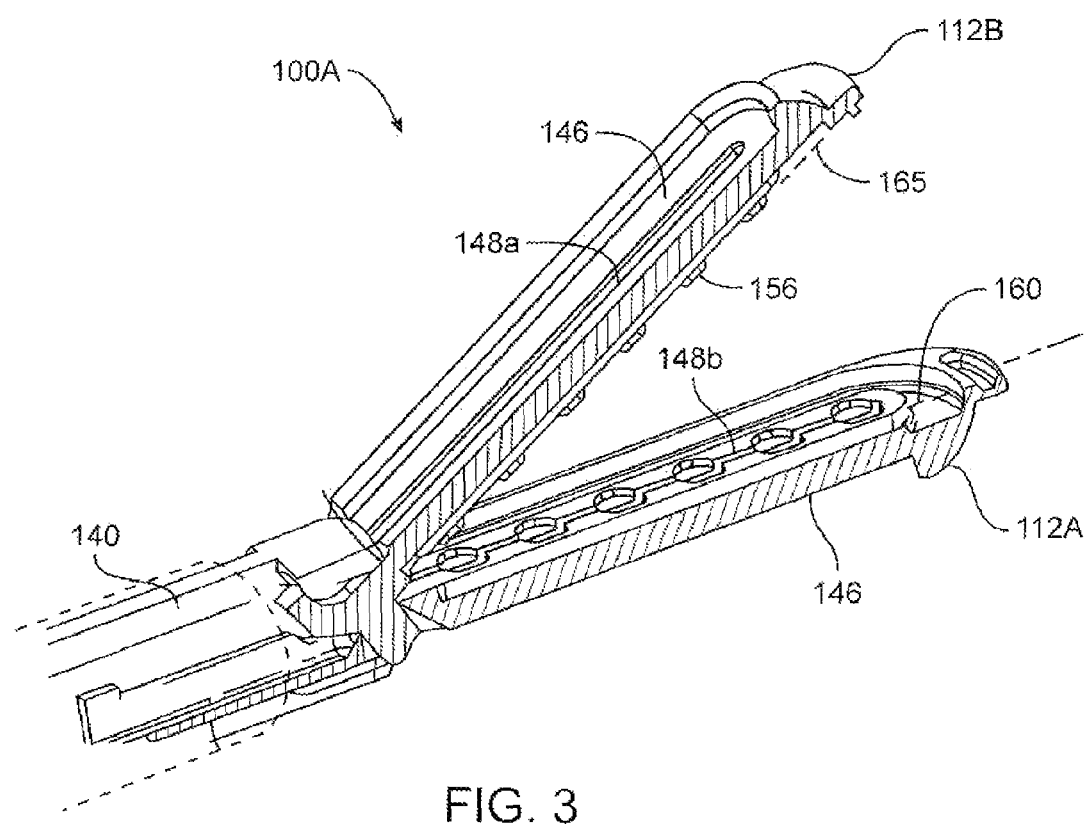
FIG. 3 is cut-away view of an exemplary Type "A" jaw structure similar to that of FIG. 2 with the PTC surfaces removed or in phantom view.
Figure 4:
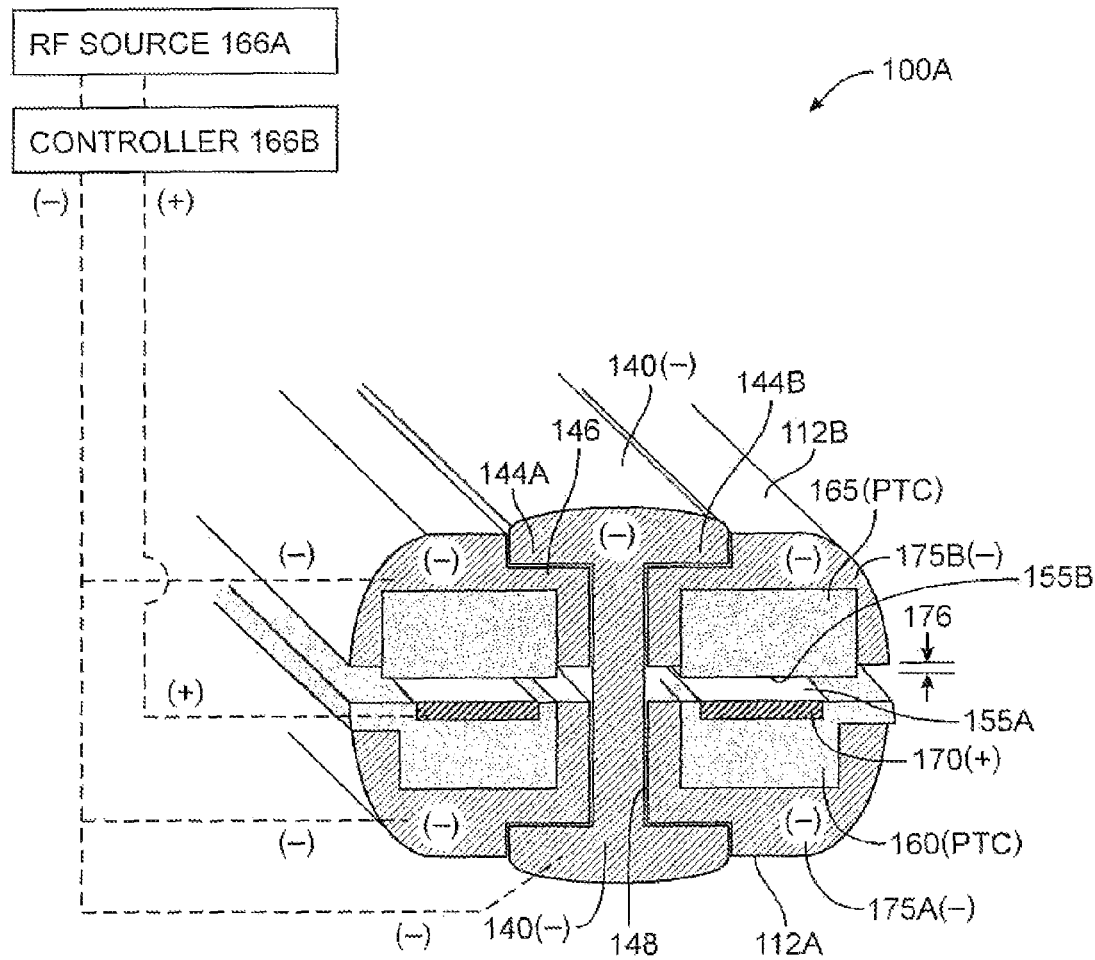
FIG. 4 is a schematic sectional view of the jaw structure of FIGS. 2 and 3 taken along line 4-4 of FIG. 1 showing the PTC matrices in each jaw together with the series and parallel circuits.

1. Type "A" jaw structure for welding tissue. FIGS. 2, 3 and 4 illustrate an exemplary working end of an embodiment of a surgical grasping instrument. The working end is adapted for transecting captured tissue and for contemporaneously welding the captured tissue margins with controlled application of RF energy. The jaw assembly 100A is carried at the distal end 104 of an introducer sleeve member 106 that can have a diameter ranging from about 2 mm. to about 20 mm. for cooperating with cannulae in endoscopic surgeries or for use in open surgical procedures. The introducer portion 106 extends from a proximal handle (not shown). The handle can be any type of pistol-grip or other type of handle known in the art that is configured to carry actuator levers, triggers or sliders for actuating the jaws and need not be described in further detail. The introducer sleeve portion 106 has a bore 108 extending therethrough for carrying actuator mechanisms for actuating the jaws and for carrying electrical leads for delivery of electrical energy to electrosurgical components of the working end.

As can be seen in FIGS. 2 and 3, the jaw assembly 100A has first (lower) jaw element 112A and second (upper) jaw element 112B that are adapted to close or approximate about axis 115. In various embodiments, the jaw elements can both be moveable or a single jaw can rotate to provide the jaw-open and jaw-closed positions. In the exemplary embodiment of FIGS. 2 and 3, the upper jaw is moveable relative to the introducer portion 106 and lower jaw.

As can be seen in FIGS. 2, 3 and 4, the opening-closing mechanism of jaw assembly 100A can be configured to apply very high compressive forces on tissue utilizing cam mechanisms having a reciprocating "I-Beam" member 140. The cam mechanism can be any well known in the art. The engagement surfaces further provide a positive engagement of camming surfaces (i) for moving the jaw assembly to the (second) closed position to apply very high compressive forces, and (ii) for moving the jaws toward the (first) open position to apply substantially high opening forces for "dissecting" tissue. This feature can be configured to allow the surgeon to insert the tip of the closed jaws into a dissectable tissue plane—and thereafter open the jaws to apply such dissecting forces against tissues. Many prior art instruments are spring-loaded toward the open position and may not be useful for dissecting tissue.

In the embodiment of FIGS. 2, 3 and 4, the reciprocating "I-Beam" member 140 is actuatable from the handle of the instrument by any suitable mechanism, such as a lever arm, that is coupled to a proximal end 141 of member 140. The proximal end 141 and medial portion of member 140 are dimensioned to reciprocate within bore 108 of introducer sleeve 106. The distal end portion 142 of reciprocating "I-Beam" member 140 carries first (lower) and second (upper) continuous laterally-extending flange elements 144A and 144B that are coupled by an intermediate transverse element 145. The flange elements 144A and 144B slide in a recessed slot portion 146 in each of the upper and lower jaw (see FIGS. 3 and 4) wherein the sliding contact of the lateral edges of flanges 144A and 144B and side of the recessed slot portion 146 function to prevent lateral flexing of the jaws. This effect of providing a reciprocating "I-Beam" member 140 that defines lateral surface portions that engage lateral edge portions of the jaws to prevent lateral jaw flexing was first disclosed in co-pending U.S. patent application Ser. No. 10/079,728 filed Feb. 19, 2002 titled Jaw Structure for Electrosurgical Systems and Techniques for Sealing Tissue, which is fully incorporated herein by reference. The transverse element 145 is adapted to transect tissue captured between the jaws with a sharp leading blade edge 147 (FIG. 2). The transverse element 145 and blade edge 147 slide within channels 148 (collectively) in the paired first and second jaws to thereby open and close the jaws. The camming action of the reciprocating member 140 and jaw surfaces is described in complete detail in co-pending Provisional U.S. Patent Application Ser. No. 60/347,382 filed Jan. 11, 2002 titled Jaw Structure for Electrosurgical Instrument and Method of Use, which is fully incorporated herein by reference.

In FIGS. 3 and 4, the first and second jaws 112A and 112B close about an engagement plane 150 and define tissue-engaging surface layers 155A and 155B that contact and deliver energy to engaged tissues from electrical energy means as will be described below. The jaws can have any suitable length with teeth or serrations 156 for gripping tissue (FIGS. 2 and 3). One preferred embodiment of FIGS. 2 and 3 provides such teeth 156 at an inner portion of the jaws along channels 148a and 148b, thus allowing for substantially smooth engagement surface layers 155A and 155B laterally outward of the tissue-gripping elements. The axial length of jaws 112A and 112B indicated above can be any suitable length depending on the anatomic structure targeted for transection and sealing and typically will range from about 10 mm. to about 50 mm. The jaw assembly can apply very high compression over much longer lengths, for example up to about 200 mm., for resecting and sealing organs such as a lung or liver. The scope of the invention also covers jaw assemblies configured for use with an instrument used in micro-surgeries wherein the jaw length can be about 5.0 mm or less.

In the exemplary embodiment of FIGS. 2, 3 and 4, the tissue-engaging surface 155A of the lower jaw 112A is adapted to deliver energy to tissue, at least in part, through a variably resistive PTC matrix 160 corresponding to the invention. The tissue-contacting surface 155B of upper jaw 112B preferably carries a similar type of PTC matrix 165 together with conductive electrode surface portions as will be described below. Alternatively, the engagement surfaces of the jaws can carry any of the PTC matrix and electrode components disclosed in co-pending U.S. patent application Ser. No. 10/032,867 filed Oct. 22, 2001 titled Electrosurgical Jaw Structure for Controlled Energy Delivery and U.S. patent application Ser. No. 10/308,362 filed Dec. 3, 2002 titled Electrosurgical Jaw Structure for Controlled Energy Delivery, (now U.S. Pat. No. 6,770,072) both of which are fully incorporated herein by reference.

It has been found that very high compression of tissue combined with controlled RF energy delivery is optimal for welding the engaged tissue volume contemporaneous with transection of the tissue. Preferably, the engagement gap g between the engagement planes ranges from about 0.0005" to about 0.050" for reducing the engaged tissue to the thickness of a membrane. More preferably, the gap between the tissue-engaging surfaces 155A and 155B ranges from about 0.001" to about 0.005".

Turning now to a discussion of the electrosurgical functionality of embodiments of the invention, FIGS. 2 and 4 illustrate the tissue-engaging surfaces 155A and 155B of jaws 112A and 112B. The opposing tissue-engaging surfaces can carry variable resistive positive temperature coefficient (PTC) bodies or matrices 160 and 165 together with opposing polarity conductors (electrode portions) that are coupled to RF source 166A and controller 166B in series and parallel circuit components (see block diagram of FIG. 5A).

In FIG. 2, it can be seen that lower jaw 112A carries a conductor (electrode) element 170 that is indicated (for convenience) with a positive polarity (+). The element 170 extends in a "U" shape about the distal end of the blade-receiving slot 148 and is coupled to RF source 166A. FIGS. 2 and 4 show the conductor element 170 embedded in the surface of PTC body 160 with inner and outer portions 172a and 172b of the PTC body intermediate the positive polarity conductor 170 and the negative polarity lower jaw body indicated at 175A (see FIG. 2). FIG. 4 shows that the RF source 166A is further coupled to the upper jaw indicated at negative polarity body 175B. In one embodiment, the PTC body 165 in the upper jaw extends outwardly a slight dimension indicated at 176 from negative polarity body 175B.

In a preferred embodiment, the PTC conductive-resistive matrix 160 is a variably resistive body that comprises a polypropylene or a medical grade silicone polymer that is doped with conductive particles (e.g. carbon). The novel use of PTC materials in electrosurgical working ends is described in co-pending U.S. patent application Ser. No. 10/351,449 filed Jan. 22, 2003 titled Electrosurgical Instrument and Method of Use (now U.S. Pat. No. 7,112,201); and Ser. No. 10/032,867 filed Oct. 22, 2001 titled Electrosurgical Jaw Structure for Controlled Energy Delivery (now U.S. Pat. No. 6,929,644), both of which are incorporated herein by reference. Polymer positive temperature coefficient (PTC) materials are known in the field of overcurrent protection devices that will "trip" and become resistant when a selected trip current is exceeded.

Various embodiments of PTC compositions can be fabricated from a non-conductive base polymer that is doped with conductive particles and exhibits two phases that define greater and lesser conductive properties. The first phase of the base polymer exhibits a crystalline or semi-crystalline state where the polymer molecules form long chains and are arranged in a more ordered architecture. When the temperature of the PTC is elevated, the polymer molecules maintain the crystalline architecture or structure—but eventually transition to an at least partly amorphous phase from the crystalline state. In the amorphous state, the molecules are aligned more randomly, and there typically is a slight increase in volume so that actual PTC geometry is altered. The non-conductive base polymer is combined with a dispersed, highly conductive particles, e.g., carbon nanoparticles to form a PTC matrix. In the crystalline phase of the polymer, the carbon particles are packed into the crystalline boundaries and form multiple conductive paths across the PTC. In this low temperature crystalline state, the polymer-carbon matrix is engineered to have a predetermined low resistance. For the purposes of the present invention, passive heat conduction from ohmically heated tissue can elevate the temperature of the PTC matrix. As long as the temperature increase in does not cause a phase change in the polymer, current will flow unimpeded. However, when the temperature of the PTC matrix is elevated to a selected temperature, called a switching range herein, the temperature will cause a phase change in the polymer. The crystalline structure of the polymer will disappear, and the carbon chains that allow for conduction across the PTC matrix will be broken resulting in an extraordinary increase in resistance. The polymer-carbon matrix can define a resistance measured in milliohms or ohms before the phase change. After the phase change, the PTC matrix' resistance can be measured in megaohms. Current flow can be reduced accordingly or terminated which is used to advantage in the present invention. Further, the modulation of current flow will be highly localized across the engagement surfaces of the PTC matrix.

Figure 6:
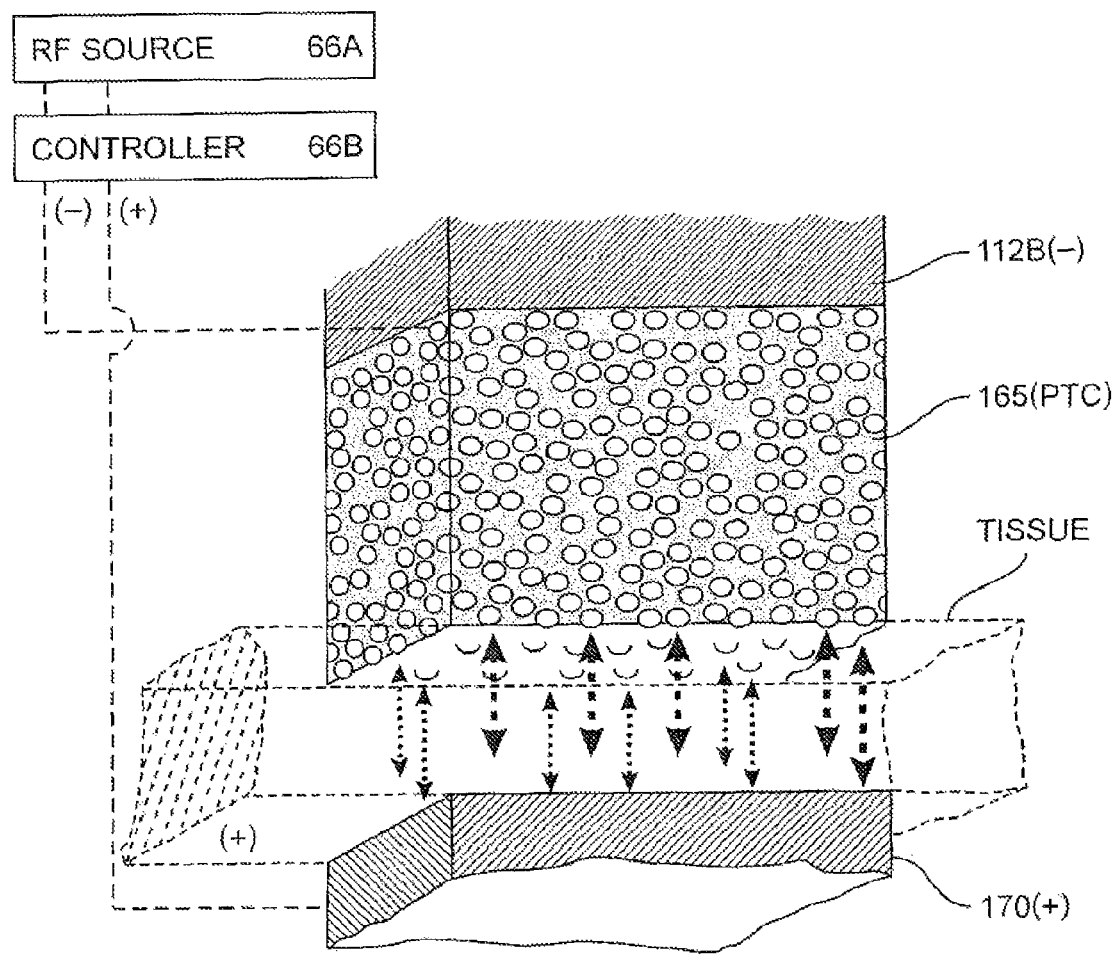
FIG. 6 is a greatly enlarged sectional view of the PTC body of an exemplary Type "A" jaw structure showing current flows in engaged tissue.

In FIG. 6, the functioning of a PTC matrix 165 in combination with an active electrode 170 (cf. FIG. 4) is illustrated wherein the localized modulation of current flow and ohmic heating in captured tissue is illustrated. The functioning of such a PTC engagement surface is more fully described in co-pending U.S. patent application Ser. No. 10/351,449 filed Jan. 22, 2003 titled Electrosurgical Instrument and Method of Use which is fully incorporated herein by reference.

Figure 5A:
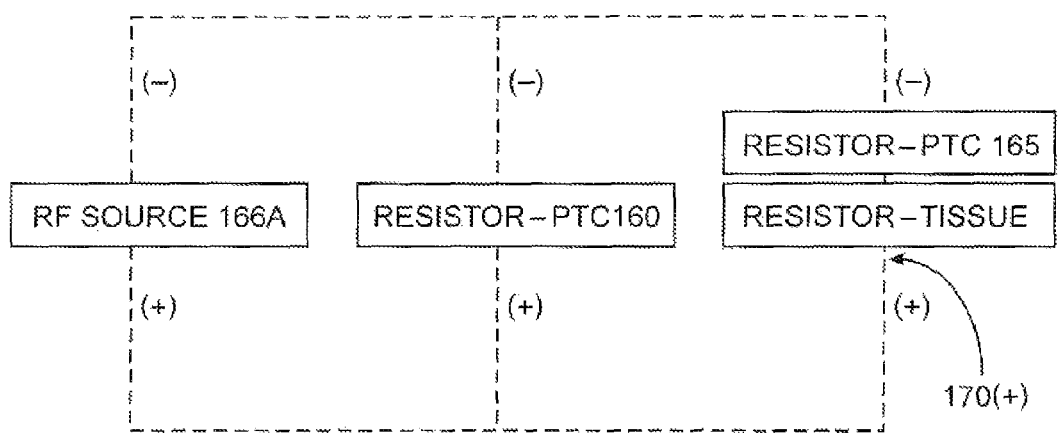
FIG. 5A is a block diagram of the series and parallel electrical circuit components of the working end of FIGS. 2, 3 and 4.
Figure 5B:
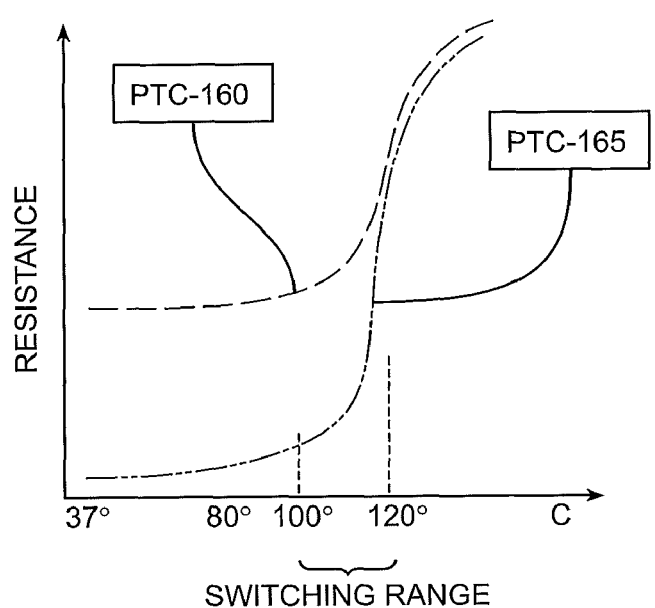
FIG. 5B is a diagram of the resistance-temperature curves of the two PTC bodies of the working end of FIGS. 2, 3 and 4.

It has been found that two differently performing PTC matrices 160 and 165 (FIG. 4) in combination with the series and parallel circuitry of FIGS. 4 and 5 allows for very uniform thermal effects in tissue to denature tissue proteins and cause high strength welds. In one embodiment, the matrix 165 in upper jaw 112B is engineered to exhibit unique resistance vs. temperature characteristics that is represented by the positively-sloped temperature-resistance curve PTC-165 of FIG. 5B. The matrix 165 maintains a very low base resistance over a selected base temperature range with a dramatically increasing resistance above a selected narrow temperature range (switching range) that can be any 10° range between about 80° C. and 120° C.

In contrast, the PTC matrix 160 in lower jaw 112A is designed to have a resistance vs. temperature characteristics with a much "higher" initial base resistance. The PTC matrix 160 maintains this "higher" base resistance over a similar temperature range as matrix 165. The PTC matrix indicated at PTC-160 in FIG. 5B exhibits a dramatically increasing resistance above its selected switching range.

In use, it can be understood that when tissue is engaged between the jaws (see FIG. 4), energy delivery to conductor element 170 embedded in PTC matrix 160 in lower jaw 112A will initially cause current flow through the hydrated, conductive tissue to PTC matrix 165 in the opposing (upper) jaw since it maintains a very low base resistance (FIG. 5B). Some current flow also will follow conductive paths to lateral negative polarity portions of the upper jaw and the negative polarity "I-Beam" 140. RF energy delivery to conductor element 170 will not cause current flow through adjacent PTC matrix 165 since it maintains the "higher" base resistance as indicated in FIG. 5B.

Figure 1A:
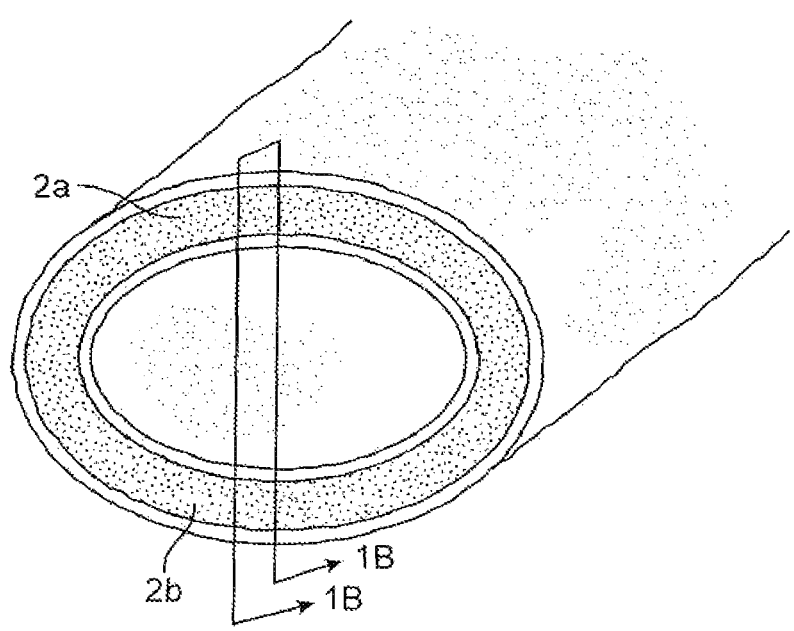
FIG. 1A is a view of a blood vessel targeted for welding.
Figure 1B:
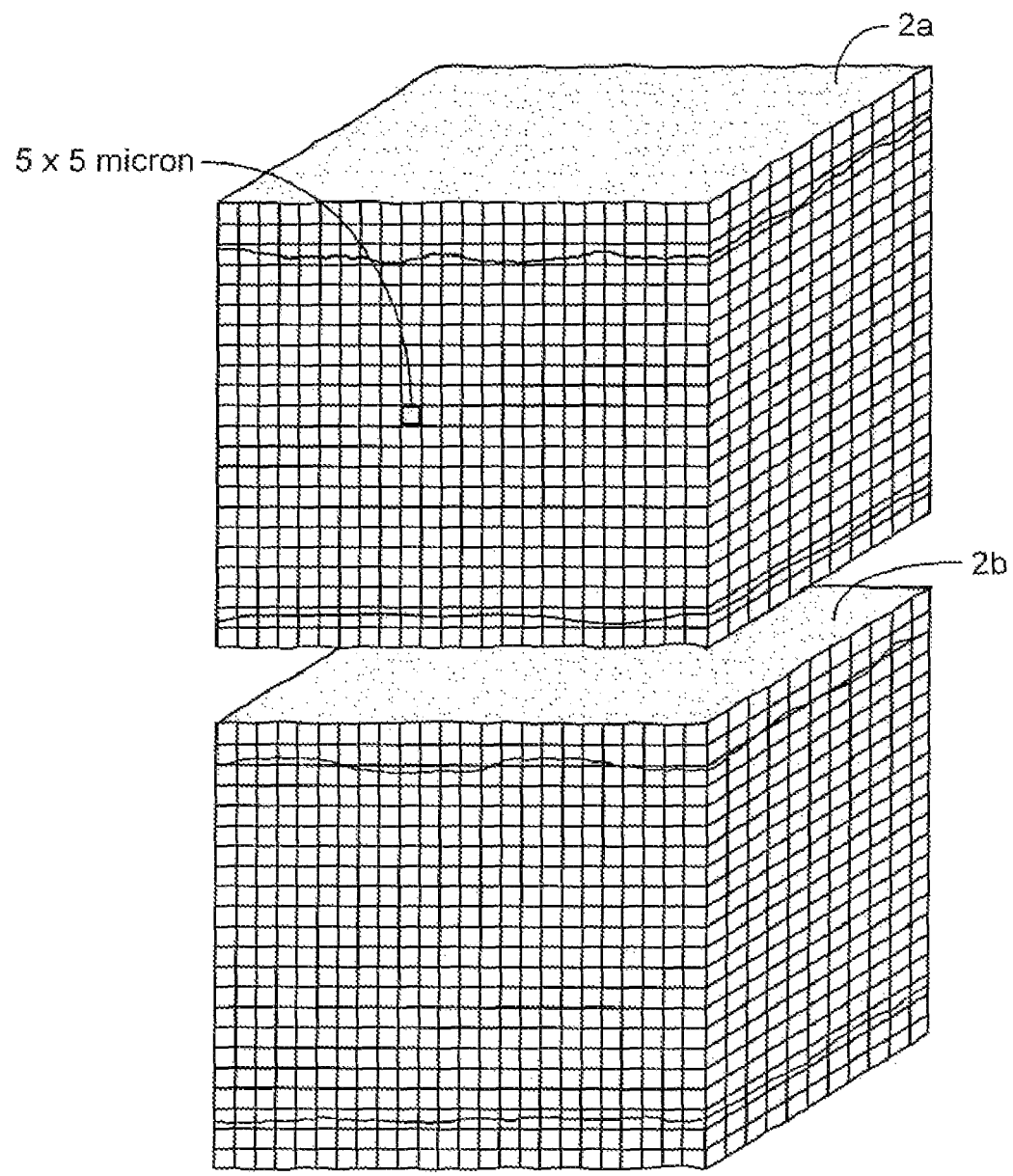
FIG. 1B is a greatly enlarged sectional view of opposing wall portions of the blood vessel of FIG. 1A taken along line 1B-1B of FIG. 1A.
Figure 1C:
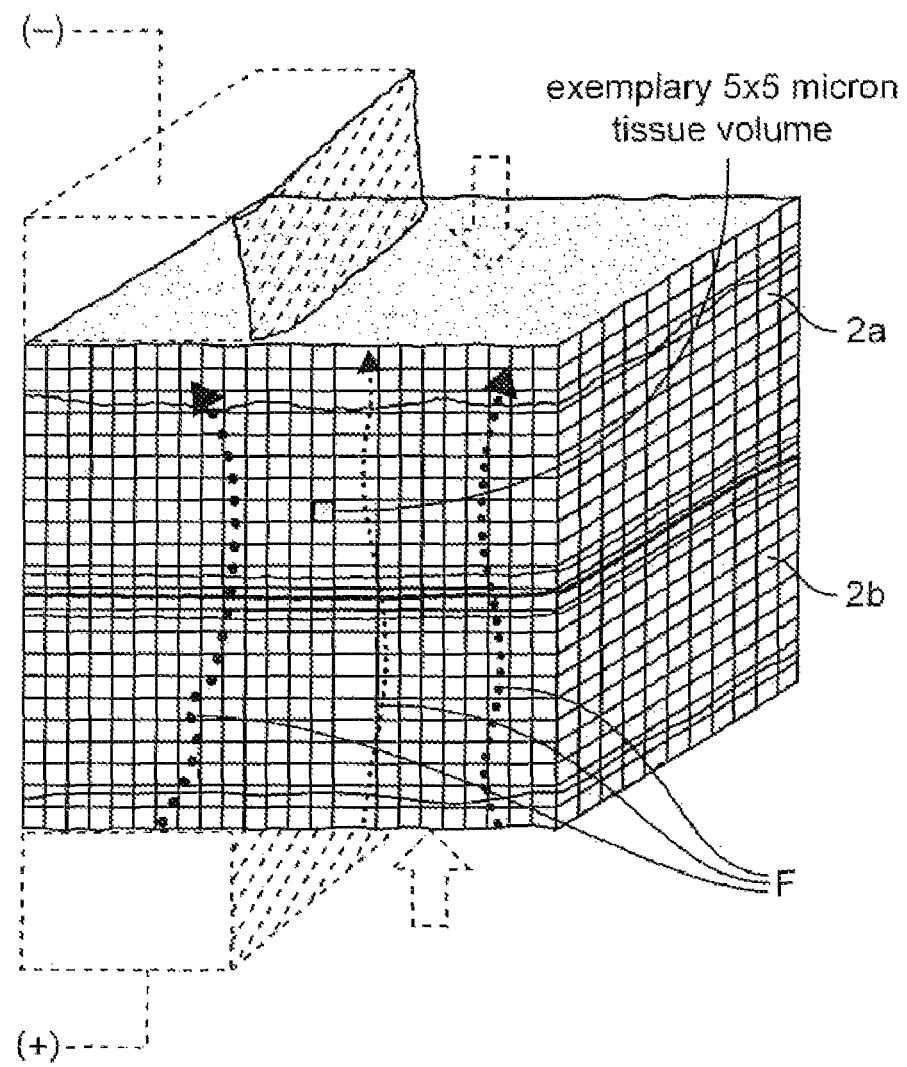
FIG. 1C is a graphic representation of opposing walls of a blood vessel engaged by prior art electrosurgical jaws showing random paths of current (causing ohmic heating) across the engaged tissue between opposing polarity electrodes.
Figure 1D:
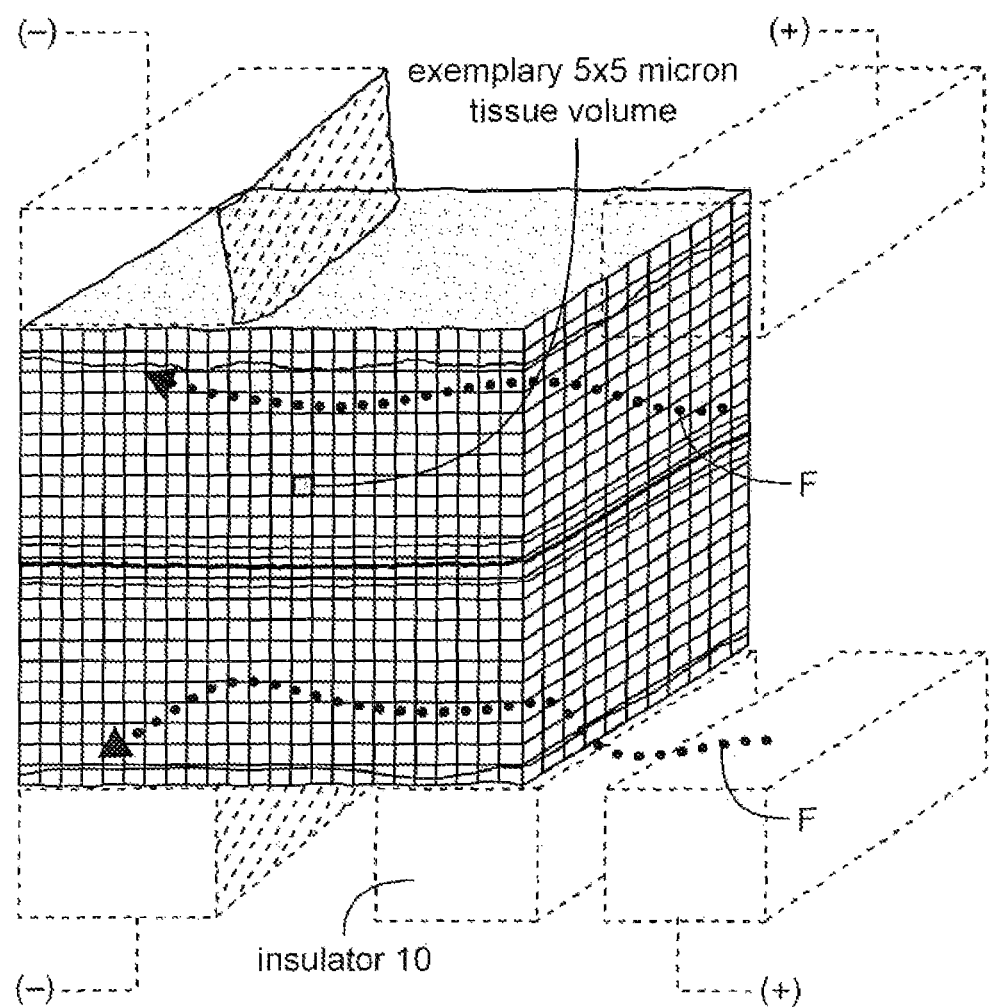
FIG. 1D is a graphic representation of a blood vessel engaged by prior art electrosurgical jaws with an insulator between opposing polarity electrodes on each side of the tissue showing random paths of current (ohmic heating).

Thus, initial RF energy delivery to active conductor element 170 in FIG. 4 will cause maximum ohmic heating in the engaged tissue—until heat from the tissue is conducted back to the PTC matrix 165 in the upper jaw 112B to then cause the PTC material 165 to reach its switching range (FIG. 5B). Referring to FIGS. 4 and 5A, it can then be understood that the series and parallel circuits will cause current flow from active conductor element 170 across the lower jaw's PTC matrix 160. Thereafter, as can be seen in FIG. 5A, the RF energy delivery will be modulated between the series and parallel circuit portions as the temperatures of the two PTC matrices 160 and 165 are modulated in response to tissue temperature. It should be appreciated that the above-described modulation of ohmic heating in tissue will occur about highly-localized portions of the engagement surfaces 155A and 155B thus making the jaw surfaces function effectively as hypothetical pixilated surfaces. In other words, ohmic heating will be independently controlled about each pixel no matter the scale of the hypothetical pixels (cf. FIG. 1D).

Figure 7:
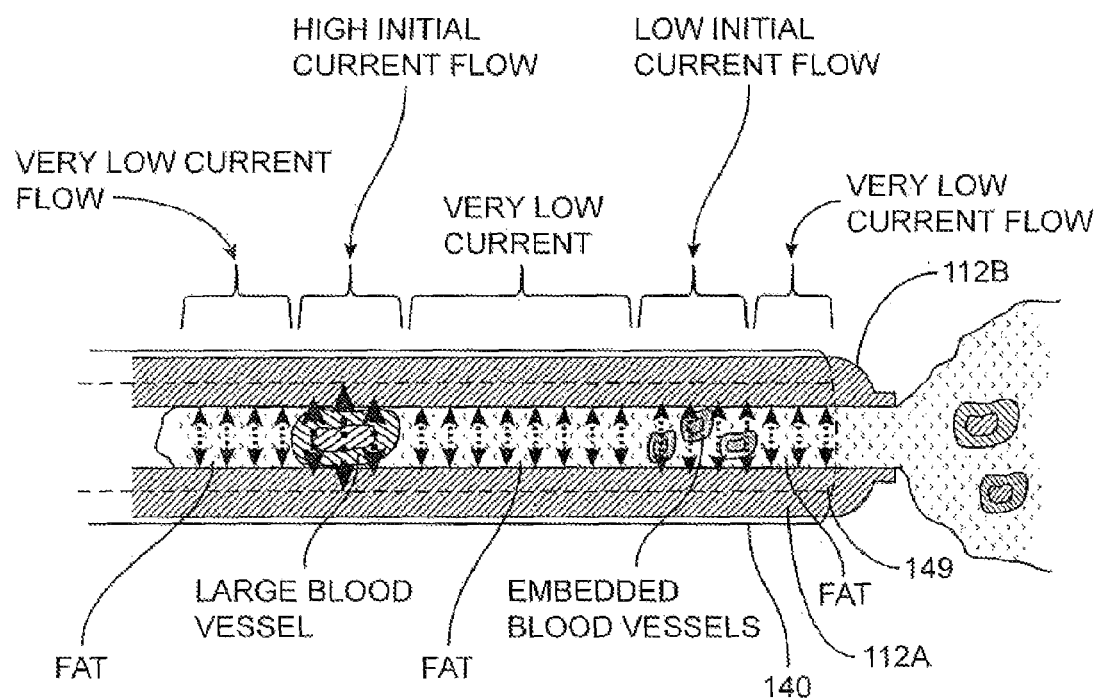
FIG. 7 is a schematic sectional view of the exemplary Type "A" jaw structure engaging and causing controlled ohmic heating in a tissue bundle of disparate anatomic structures.

Referring now to FIG. 7, another aspect and method of the invention is illustrated schematically wherein the opposing jaws 112A and 112B engage a tissue mass or bundle of differentiated tissues as often must be transected in open and endoscopic surgeries. A longitudinal sectional not-to-scale view of jaws 112A and 112B and a tissue bundle are shown, for example, wherein the hypothetical tissue bundle contains insulative fatty tissues, large blood vessels and smaller embedded blood vessels. The gap between the jaws in an actual jaw structure would be very small and is not-to-scale in FIG. 7. Further the PTC matrices and active electrode 170 are not shown distinctly. In real tissue, the bundle would contain fascia, ligamentous tissues, etc. and exhibit a wide range of hydration levels, electrolyte levels, etc. that would locally alter tissue resistivity. For convenience, three tissue types with three resistance levels are shown. As indicated by the microcurrents in FIG. 7, the initial delivery of RF energy to active conductive electrode 170 (lower jaw 112A; see FIG. 4) will self-modulate energy densities across the various tissues to PTC matrix 165 (upper jaw 112B; see FIG. 4) according to the impedance of each engaged tissue type. This effect of utilizing the very low-ohm PTC matrix 165 thus allows the regions (or pixels) of the engagement surface 155B of PTC matrix 165 to be elevated in temperature very rapidly adjacent highly resistive tissues such as the fatty tissues. As a result, this tissue will not have active RF density and ohmic heating therein and will not desiccate or char. At the same time, the weldable vascular tissue will be subject to much greater initial ohmic heating which is desirable in creating an effective weld.

Figure 8A:
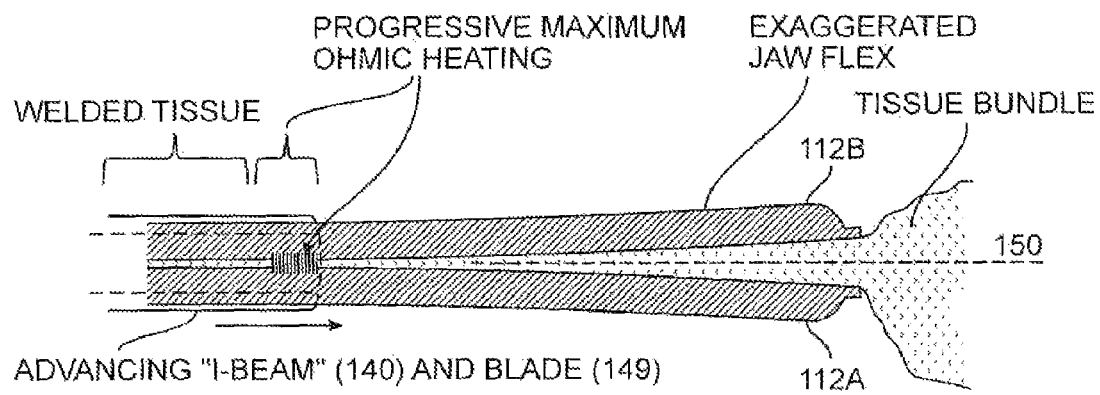
FIGS. 8A-8C are schematic sectional views of the exemplary Type "A" jaw structure progressively engaging, transecting and welding the margins of the transected tissue bundle.
Figure 8B:
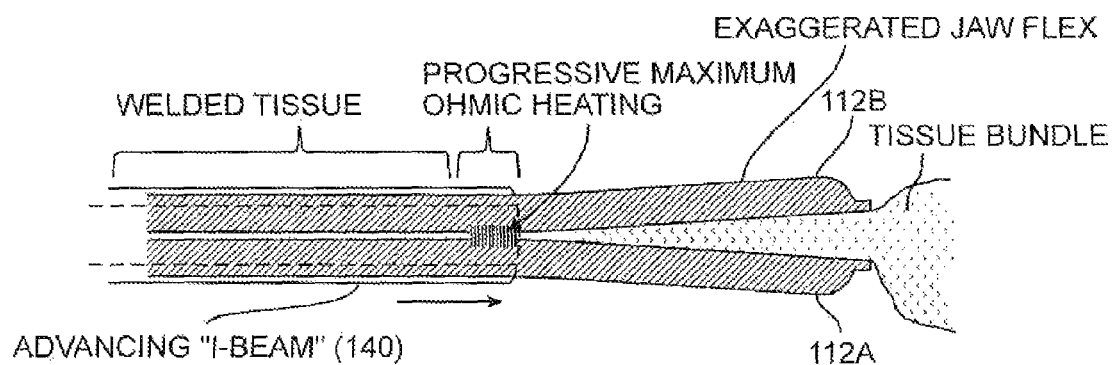
Figure 8C:
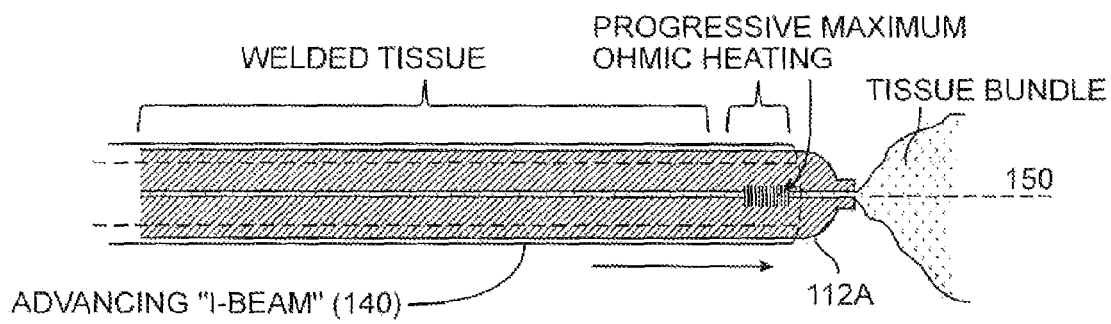

Referring now to FIGS. 8A-8C, another aspect and method of the invention is illustrated schematically wherein the opposing jaws 112A and 112B are adapted for (i) progressive engagement, compression and transection of tissue bundles; (ii) contemporaneous and progressive delivery of RF energy to the transected tissue margins; and (iii) wherein the RF energy delivery causes a tissue weld to be progressively created over a short or elongated transection line.

More in particular, the inventive jaw structure 100A clamped over tissue with RF delivery in one step contemporaneous with jaw closure and tissue transection. Prior art RF coagulation instruments in all cases (it is believed) use essentially three steps: (i) closing the jaw mechanism, (ii) applying RF energy to tissue, and (iii) actuating a blade member to transect the tissue. In contrast, the jaw structure of the present invention accomplishes all these functions in a single step. As can be understood from FIG. 4, the jaw structure also is unique in that it is not possible to create a short circuit across the jaws—since the PTC 165 immediately would switch and cooperate with the other PTC 160 to carry the current through the cooperating circuit component.

It has been found that by applying RF energy by PTC modulated means as tissue is engaged and cut, the more proximal tissue is dehydrated to some extent as it is welded thus allowing the tissue to be easily compressed to a thin membrane. In FIGS. 8A-8C, the jaws are shown with a greatly exaggerated flex characteristics to illustrate, in effect, what has been found to occur. The "I-Beam" 140 can compress the tissue dramatically as it is progressively dehydrated and welded—thus a very small jaw structure in a 5 mm. diameter device can chomp down on, weld and transect very thick tissue bundles, even up to ½ inch or 1 inch thick. The highest ohmic heating progresses in a "front" across the tissue and is automatically modulated by the PTC matrices and series/parallel circuit as described above. The jaw structure further allows the surgeon tactile feedback of the tissue welding process as the advancement of the "I-Beam" 140 indicates that the tissue is welded.

Thus, an embodiment of a method of the invention for welding tissue can include the microscale modulation of ohmic "active" heating in engaged tissue as depicted in FIG. 6 combined with the more macroscale modulation of ohmic heating in FIGS. 8A-8C—all at the same time that regional ohmic tissue heating self-modulates in response to tissue type (impedance) as depicted in FIG. 7. This functionality is provided by the different cooperating PTC components 160 and 165 of the jaw structure. Thus, in a broad embodiment, the electrosurgical working end 100A defines first and second energy-delivery surface elements coupled in series to an RF source, the first surface conductive element 170 overlying and electrically coupled to a first PTC body 160, wherein the first surface element and first PTC body 160 are coupled in parallel to the RF source. The second energy delivery surface 165 also is a PTC composition.

Figure 9:
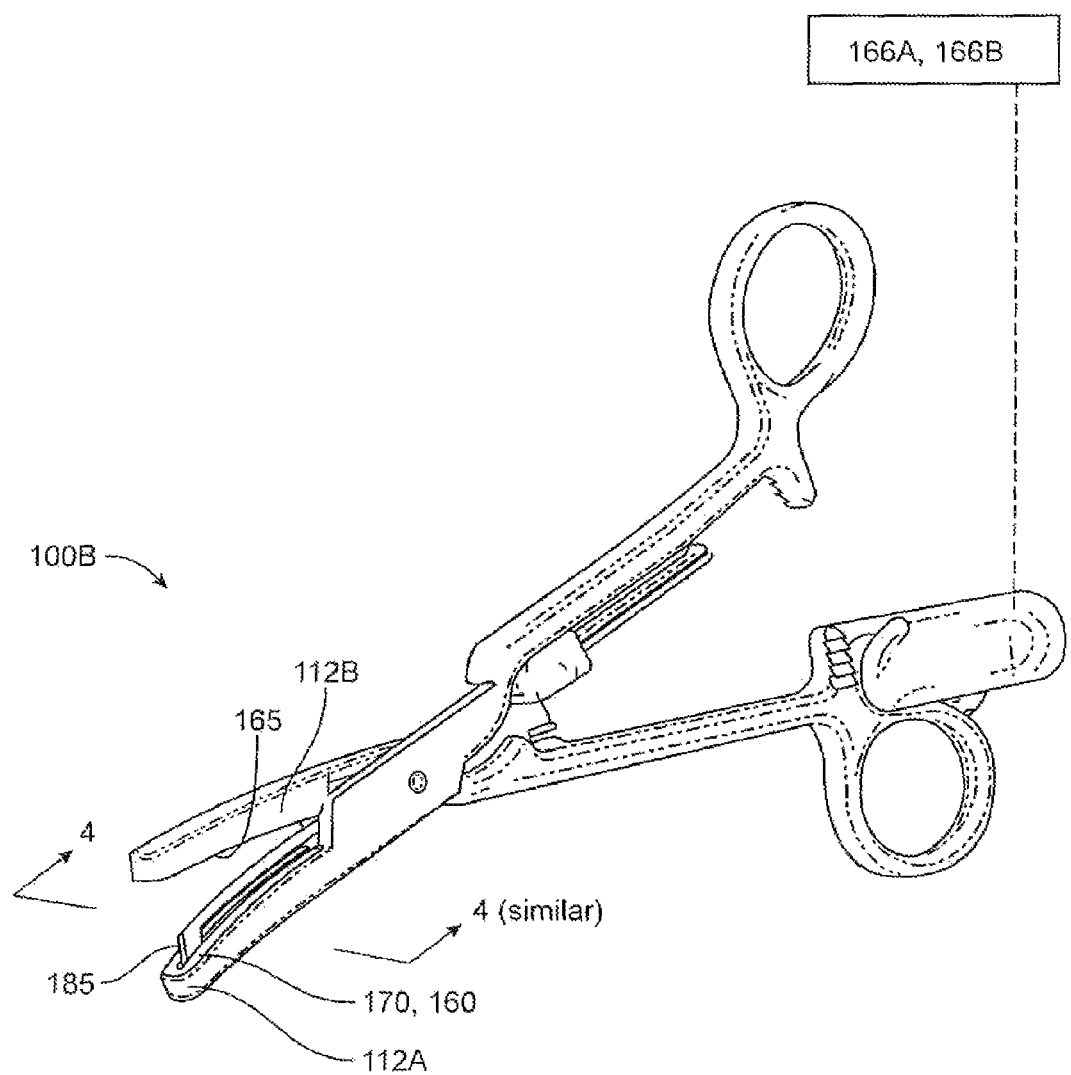
FIG. 9 is a perspective view of an alternative Type "A" jaw structure.

Referring now to FIG. 9, an alternative jaw structure 100B is shown with lower and upper jaws having similar reference numerals 112A-112B. The scissor-action of the jaw structure in FIG. 10 has been found to be useful for welding tissues for open procedures. The tissue transection is accomplished by a slidable blade 185. Such scissor-action of the jaws can apply high compressive forces against tissue captured between the jaws to perform the method corresponding to the invention as described above. In all other respects, the scissor-jaw instrument of FIG. 9 functions as the working end of FIGS. 2, 3 and 4. The apparatus of FIG. 9 with at least one replaceable PTC matrix was described in co-pending U.S. patent application Ser. No. 10/443,974, filed May 22, 2003 titled Electrosurgical Working End with Replaceable Cartridges, which is fully incorporated herein by reference.

Figure 10:
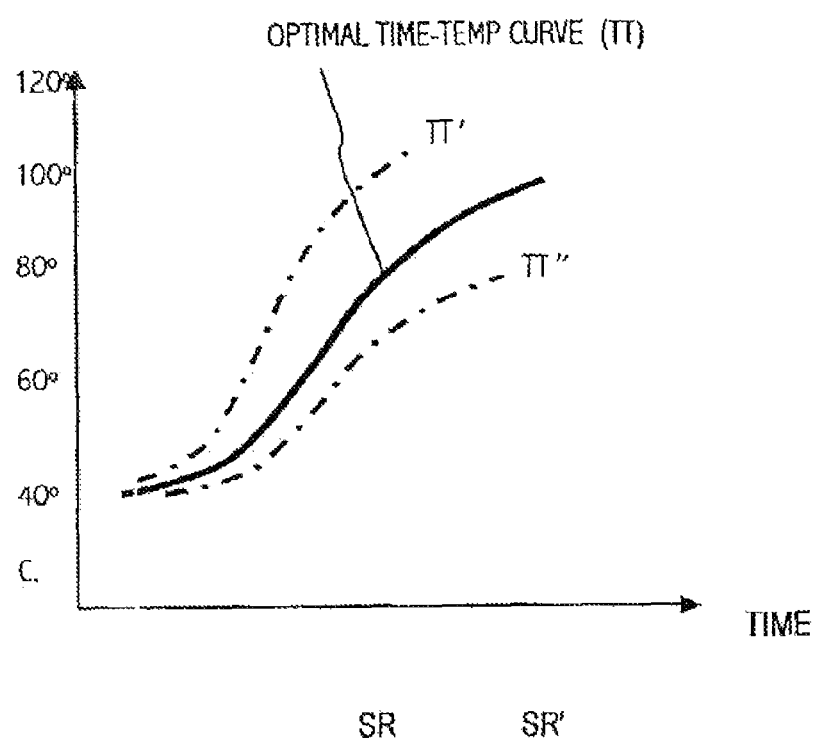
FIG. 10 is graph of time-temperature curves illustrating the objectives of a Type "B" jaw structure that utilizes control algorithms for standardizing weld times.

2. Type "B" electrosurgical system. FIG. 10 describes a system and method of the invention for automatically controlling termination of energy delivery to the jaw structure 100A of FIGS. 2, 3 and 4. It has been found that an effective weld can be created in tissues very rapidly, for example, within a few seconds and it would be useful to have a "smart" control system automatically terminate or modulate RF energy delivery when the weld is satisfactory. Alternatively, it would be useful to modulate RF energy delivery to create the optimal ramp-up in tissue temperature when progressively engaging, transecting and welding tissues as depicted in FIGS. 8A-8C.

In FIG. 10, the manner of utilizing the control system to perform the method of the invention can be understood as obtaining signals from the series-parallel circuits of FIG. 5A to calculate the rate of change in tissue impedance-temperature, and modulating the RF delivery to maintain the optimal time-temperature curve TT in FIG. 10. In other words, the measured rate of change may be curve TT' or TT" in FIG. 10, and the control would adjust power to maintain the optimal time-temperature curve. Such control algorithms can be developed and the method accomplished without the use of thermocouples in the working end. Of particular interest, the above-described method of the invention allows for immediate overall RF modulation for ohmic heating—while the cooperating PTC components of the engagement surfaces modulate energy density at the regional or pixilated level to prevent tissue desiccation and charring. Thus, this method of the invention can be used to standardize tissue welding no matter the type of tissue engaged—wherein the controller applies energy to accomplish the weld in a selected time, for example, 5 seconds, 7 seconds or 10 seconds.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further, variations will be apparent to one skilled in the art in light of this disclosure and are intended to fall within the scope of the appended claims. Also, elements or steps from one embodiment can be readily recombined with one or more elements or steps from other embodiments.

What is claimed is:

1. An electrosurgical instrument for applying energy to a body structure, the instrument comprising first and second jaws carrying respective first and second energy-delivery elements coupled to an RF source by a first circuit component, the first energy-delivery element coupled to a resistive body in the first jaw, wherein the first energy-delivery element and the resistive body are coupled the RF source by a second circuit component, and wherein the second energy-delivery element is a positive temperature coefficient (PTC) composition and the resistive body is a PTC composition and the second energy-delivery element PTC composition and the resistive body PTC composition define different temperature-impedance curves.

2. An electrosurgical instrument as in claim 1, wherein the first circuit component comprises a series circuit when engaging body structure.

3. An electrosurgical instrument as in claim 1, wherein the second circuit component comprises a parallel circuit.

4. An electrosurgical instrument as in claim 1, wherein the second energy-delivery element PTC composition defines a substantially low impedance in a 40° C. to 60° C. range.

5. An electrosurgical instrument as in claim 1, wherein the second energy-delivery element PTC composition defines a substantially lower impedance in a 40° C. to 60° C. range than the resistive body PTC composition in a similar temperature range.

6. An electrosurgical instrument comprising first and second jaws coupled to an RF source and actuatable between a first open position and a second closed position, the jaws in a closed position define an engagement gap, wherein the first jaw carries a first energy-delivery element and the second jaw carries a second energy-delivery element of PTC composition, the first energy-delivery element coupled to a resistive body PTC composition in the first jaw, and the second energy-delivery element PTC composition and the resistive body PTC composition define different temperature-impedance curves.

7. An electrosurgical instrument as in claim 6, wherein the engagement gap ranges from about 0.0005 inches to about 0.050 inches.

8. An electrosurgical instrument as in claim 6, wherein the engagement gap ranges from about 0.001 inches to about 0.005 inches.

9. An electrosurgical instrument as in claim 6, wherein the first and second energy-delivery elements are coupled to the RF source by a first circuit configuration.

10. An electrosurgical instrument as in claim 6, wherein the first energy-delivery element and the resistive body PTC composition are coupled to the RF source by a second circuit configuration.

11. An electrosurgical instrument as in claim 6, wherein the first circuit configuration comprises a series circuit when engaging a body structure.

12. An electrosurgical instrument as in claim 10, wherein the second circuit configuration comprises a parallel circuit.

13. An electrosurgical instrument as in claim 6, further comprising a axially-extending member that is actuatable from a first retracted position to a second extended position, wherein actuation of the axially-extending member toward the second extended position actuates the first and second jaws toward the second closed position.

14. An electrosurgical instrument as in claim 13, wherein the axially-extending member carries a blade member for transecting tissue.

15. An electrosurgical instrument as in claim 13, wherein the axially-extending member is connected to the RF source.

16. An electrosurgical instrument as in claim 6, wherein the second energy-delivery element PTC composition defines a substantially low impedance in a 40° C. to 60° C. range.

17. An electrosurgical instrument as in claim 6, wherein the second energy-delivery element PTC composition defines a substantially lower impedance in a 40° C. to 60° C. range than the resistive body PTC composition in a similar temperature range.

* * * * *